United States Patent [19]

Bloos et al.

[11] Patent Number: 5,705,719
[45] Date of Patent: Jan. 6, 1998

[54] SELECTIVE REMOVAL OF PERFLUOROISOBUTYLENE FROM STREAMS OF HALOGENATED HYDROCARBONS

[75] Inventors: Jan Pieter Jacques Bloos, Delft; Tom Spoormaker, Papendrecht, both of Netherlands; Glenn Fred Leverett, Vienna, W. Va.

[73] Assignee: E. I. Du Pont de Nemours and Company, Wilmington, Del.

[21] Appl. No.: 690,923

[22] Filed: Aug. 1, 1996

[51] Int. Cl.⁶ .................................................. C07C 17/389
[52] U.S. Cl. ............................................................ 570/179
[58] Field of Search ............................................ 570/179

[56] References Cited

U.S. PATENT DOCUMENTS

| | | | |
|---|---|---|---|
| 5,210,342 | 5/1993 | Moore | 570/179 |
| 5,600,040 | 2/1997 | Corbin et al. | 570/179 |

*Primary Examiner*—Paul F. Shaver

[57] ABSTRACT

An adsorption-desorption process using activated carbon removes perfluoroisobutylene from gaseous streams of halogenated hydrocarbons. Choice of gas and temperature profile used for desorption of adsorbed compounds and regeneration of the activated carbon facilitates concentration and removal of the perfluoroisobutylene.

18 Claims, 3 Drawing Sheets

SELECTIVE REMOVAL OF PERFLUOROISOBUTYLENE FROM STREAMS OF HALOGENATED HYDROCARBONS

FIELD OF THE INVENTION

This invention pertains to the removal of perfluoroisobutylene from process streams generated in the synthesis of halogenated compounds.

BACKGROUND OF THE INVENTION

Tetrafluoroethylene (TFE) and hexafluoropropylene (HFP) are useful as monomers for incorporation in a variety of plastic and elastomeric fluoropolymers, such as PTFE, TFE/HFP copolymers, and polymers in which either or both TFE and HFP are copolymerized with other monomers. It is well known to synthesize TFE and HFP by pyrolysis of $CF_2HCl$ (HCFC-22), as discussed, for example, in U.S. Pat. Nos. 2,551,573; 2,994,723; 3,306,940 and 3,308,174. During such pyrolysis, perfluoroisobutylene, $(CF_3)_2C=CF_2$, (PFIB) can be formed as an impurity. PFIB can also be formed during other processes, including, for example, the synthesis of fluorine-containing compounds other than HCFC-22 and the decomposition of fluorine-containing polymers. PFIB can also be present in vapors associated with products downstream from the source of PFIB, if not removed from PFIB-containing feed streams used in synthesis of those downstream products.

PFIB is extremely toxic. Consequently, if present, it should be carefully contained within process equipment handling the stream in which it was generated, and either removed from product and waste streams or detoxified in some way. Additionally, the possible presence of PFIB throughout a train of process equipment imposes demanding standards of PFIB purging and personnel protection before equipment can be opened for maintenance procedures.

A process that can be used to remove PFIB from a stream of fluorinated compounds close to the stage at which PFIB is formed, thereby eliminating PFIB residence in downstream equipment, is highly desired.

Treat in European Patent 2098 discloses a method for contacting PFIB with a solution of HF and/or HCl in liquid methanol to yield less toxic ethers.

Karwacki & Stickel at the Twentieth Biennial Conference on Carbon, Abstracts pp. 74–75 (1991), discuss the influence of moisture-laden activated carbon on the reaction of PFIB with water vapor to form tris-trifluoromethylmethane (TTFMM) and/or 3-trifluoro 2-trifluoromethylpropionic acid.

Hall et al. in Chemistry and Industry, 6 March, 145 (1989) discuss the ability of vapour filters containing activated carbon to provide respiratory protection against PFIB. The activated carbons used had apparent surface areas of about 1180 $m^2/g$, and at equilibrium with air at 80% relative humidity (RH) contained 33–43% w/w water. The several reactions believed to occur when such a filter is challenged with PFIB in air at 80% RH include a sequence that starts with hydrolysis of PFIB to hexafluoroisobutyric acid and HF, followed by reaction of the HF with PFIB to yield TTFMM.

SUMMARY OF THE INVENTION

This invention provides a process for removing perfluoroisobutylene from a gaseous stream of halogenated compounds, comprising contacting the stream with dry activated carbon for a time sufficient to achieve effective removal of PFIB. Temperatures ranging up to 60° C. are preferred when the stream contains desirable unsaturated compounds such as tetrafluoroethylene or hexafluoropropylene. Activated carbon most suitable for use in the process of this invention has a large micropore volume. Preferred carbon also has macropores.

The invention further provides processes for regenerating the activated carbon that effect further separation of perfluoroisobutylene from other compounds adsorbed from the gaseous stream by the carbon. A preferred desorption process comprises a period of desorption at a first lower temperature using an inert purge gas, followed by desorption at a second higher temperature using the same or a different purge gas. Superheated steam can advantageously be used as the second purge gas.

DETAILED DESCRIPTION OF THE INVENTION

Figure 1:
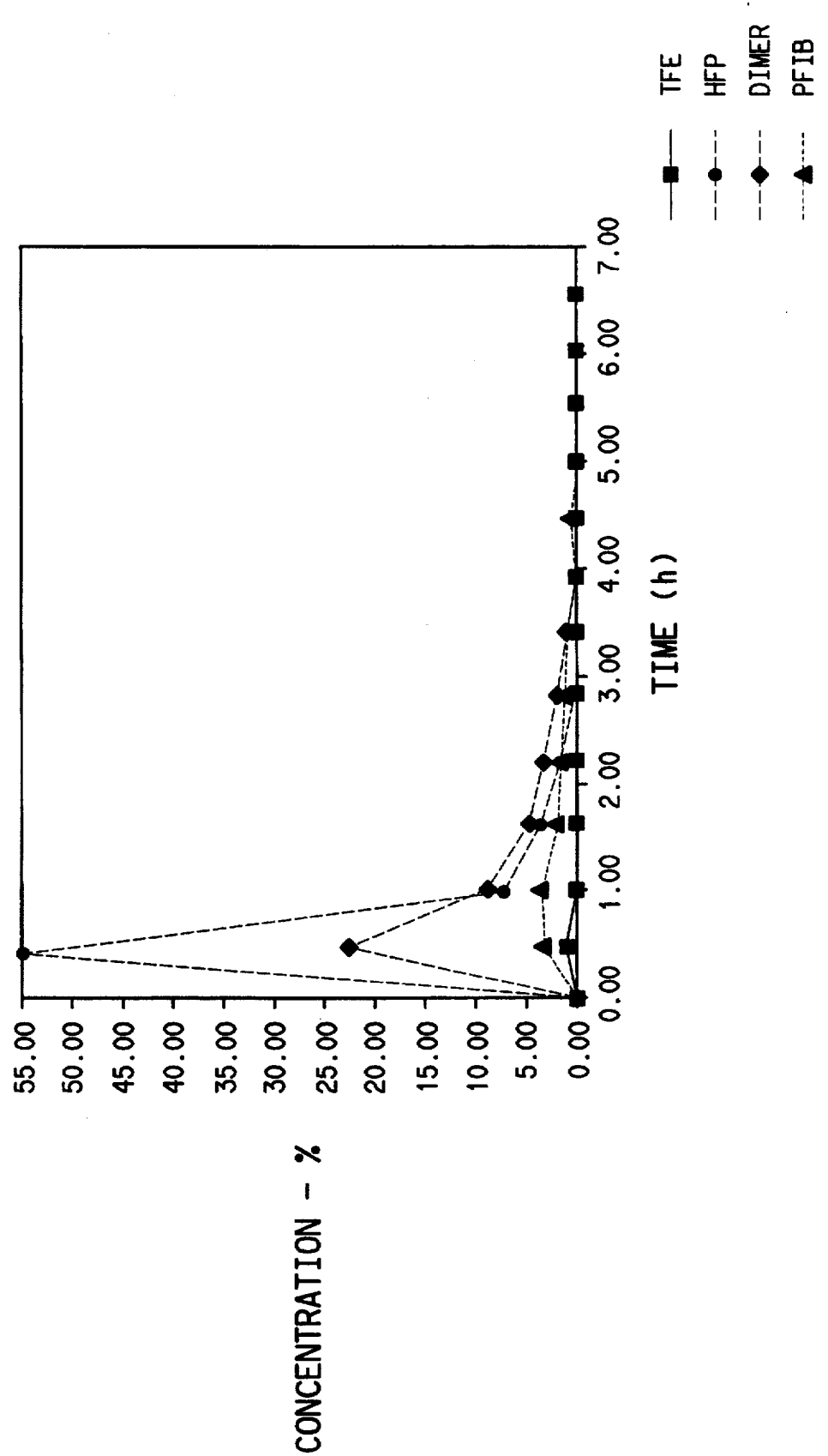
FIG. 1 shows the desorption profile for compounds adsorbed on activated carbon, using $CF_2HCl$ as the regenerating gas (Example 6).

It has been discovered that PFIB can be effectively removed from a gaseous stream, optionally with HCl and/or HF also present in the stream, by contacting the stream with activated carbon. Adsorbed PFIB, or PFIB reaction products, can be desorbed by several processes that regenerate the activated carbon for reuse. The activated carbon is surprisingly selective in adsorbing PFIB, in desorbing PFIB, and in catalyzing certain reactions of PFIB. Selectivity in adsorption can be seen, for example, in increased PFIB concentration in adsorbed compounds relative to concentration in the gaseous stream (see Example 6), and in desorption by time displacement in desorption of PFIB relative to desorption of other adsorbed compounds (see Examples 6–8).

The composition of the gaseous stream can vary. The stream can consist primarily of PFIB itself. It can have constituents that are not halogenated, provided these consitituents do not react with carbon under process conditions. Streams containing halogenated hydrocarbons in addition to PFIB are of particular interest. The halogenated hydrocarbons in the stream may be saturated or unsaturated. TFE and HFP are examples of unsaturated compounds that may be components of the stream. Octafluorocyclobutane is an example of a saturated compound that may be a component of the stream. The halogenated hydrocarbons in the stream need not be perfluorinated. However, synthesis conditions that would generate PFIB as an impurity are likely to be those designed to yield highly fluorinated products. Likewise, if decomposition is the process resulting in PFIB, the decomposing products most likely to yield PFIB would be highly fluorinated, as would other decomposition products. Chlorofluorocarbons may be present, either as major or minor components of the stream, as well as fluorohydrocarbons and chlorofluorohydrocarbons.

The gaseous stream can have components other than halogenated compounds. In particular, the stream can contain species that are considered to be relatively inert in the synthesis of halogenated compounds, including nitrogen and carbon dioxide.

The gaseous stream may have any source, with synthesis of TFE and/or HFP being of particular interest. Ideally, the stream will be subjected to the process of this invention as closely as possible to its source and to the time of its formation. Alternatively, the stream subjected to the process of this invention may be a fraction of the source stream, or the application of the process may be delayed, e.g., by accumulation or storage of the source stream or a fraction containing PFIB. Consequently, the process of this invention can be operated either continuously or on a batch basis.

The amount of PFIB in the gaseous stream can vary widely, depending on the source conditions giving rise to its presence and on processes subsequent to its generation that may result in increased or decreased concentration. Generally, the process of this invention can be applied to gaseous streams having PFIB concentration in the range 0.005–20 vol % at process temperature and pressure.

The gaseous stream may contain HCl or HF, either from the stream source, or as the result of downstream operations. For example, HCl would naturally be present in the source stream from pyrolysis of HCFC-22 to make TFE. Likewise, if one were to use $CF_3H$ as the feedstock to make TFE, HF would naturally be present. The gaseous stream fed to the activated carbon is preferably dry so that any acid component of the stream does not form aqueous acid which is very corrosive. In one aspect of the invention, adsorption of PFIB from a stream containing HCl or HF is accompanied by catalytic reaction of the PFIB with HCl or HF. If such reaction is desired, and if the concentration of HCl or HF is not high enough to satisfy the requirements of such reaction, HCl or HF can be added.

In the process of this invention, the fluorocarbon stream containing PFIB is brought into contact with a bed of activated carbon contained within a reaction chamber. The reactor is conveniently a tubular or pipe-shaped reactor into which the carbon is packed. Alternatively, other forms of reactors used for gas phase reactions can be used to practice the invention, e.g., a fluidized bed reactor.

Activated carbons typically have high surface areas in the range 500–1500 $m^2$/g as measured by $N_2$ BET. Activated carbons suitable for use in the process of this invention should have surface area of at least 800 $m^2$/g, preferably at least 1000 $m^2$/g. Surface area is high as a consequence of high pore volume, which can be as high as 450 mL/L and possibly higher, though the highest total pore volumes are not necessary for this invention. For the process of this invention, the pore volume should include a significant fraction attributable to micropores, that is, to pores with diameter less than 2 nm. Preferred activated carbon will have micropore volume that is at least 0.25×total pore volume. Micropore volume that is at least about 0.35×total pore volume is more preferred. Total pore volume is the sum of micropore (<2 nm), mesopore (2–100 nm), and macropore (>100 nm) volumes, and does not include interparticle space. See Example 5 for characterization of some activated carbons. Micropore volume can be calculated from a measured benzene adsorption isotherm using the Dubinin equation (Dubinin & Astakhov, Isv. Akad. Nauk SSSR, Set. Khim, 1971). In addition to micropores, it is advantageous for the activated carbon also to have macropores, that is, pores with diameter greater than 100 nm. Although the function of the larger pores is not understood with certainty, it is conjectured that they facilitate the transport of PFIB and/or reaction products within the carbon. Activated carbons span a spectrum from L-carbon (rich in oxygen, hydrophilic) to H-carbon (low in oxygen, hydrophobic). H-carbon is preferred. Suitable activated carbons are commercially available. The activated carbon is preferably heated prior to use to drive off adsorbed water that may be present, so that the formation of aqueous acid can be avoided.

The process stream is in contact with the activated carbon for a time sufficient to achieve effective removal of PFIB. Suitable contact time, also called residence time, will vary with other process variables such as temperature, pressure, and PFIB content in the process stream, as those smiled in the art will recognize. Contact times in the range of from 1 sec to 30 min can be used. Preferred contact times are 1–10 min. Contact time is calculated as the carbon-filled volume of the reactor divided by the volumetric flow rate of the process stream at process temperature and pressure. Absolute pressure can be 80–1000 kPa with 100–200 kPa preferred. The process can be operated in the temperature range −10° to 180° C. Temperatures in the range 10°–60° C. are preferred, especially so if the process stream contains desirable unsaturated products such as TFE or HFP.

The activated carbon functions as an adsorbant in the process of this invention and also appears to function as a catalytic substrate for the reaction of PFIB with the HCl or HF, if present. The adsorbed material may be either PFIB or a reaction product of PFIB. Certain other constituents of the gaseous stream may also be adsorbed on the carbon or dissolved in the adsorbed volume of PFIB. The selectivity of the activated carbon to the adsorbtion of PFIB and/or its reaction products is a surprising aspect of the process of this invention.

A second surprising aspect of this invention is that the bed of activated carbon can adsorb and convert, combined, a volume of PFIB that exceeds the adsorption capacity of the bed, with excess conversion product breaking through the bed. The effluent stream from the bed can contain reaction products of PFIB in concentration comparable to the concentration of PFIB in the inlet stream. If HCl is in the inlet stream, the primary reaction product is $(CF_3)_2$—CH—$CF_2Cl$ (HCFC-328lmz). If HF is present, the primary reaction product is $(CF_3)_3$—CH (TTFMM).

When the bed of activated carbon has adsorbed a volume of PFIB or reaction product approaching the capacity of the bed, which is limited by its pore volume, the carbon can be regenerated as an alternative to replacement by new carbon. The activated carbon can be regenerated at temperatures in the range 10°–500° C., either under vacuum or in an inert atmosphere at pressures in the range 10–2000 kPa absolute, preferably 20–120 kPa absolute. Regeneration in an inert atmosphere is preferred, and preferably with the inert gas sweeping through the bed of carbon. As used herein, "inert" means essentially inert with respect to the adsorbed compounds under regeneration conditions. Preferred inert gases include nitrogen or a low-boiling halocarbon such as HCFC-22, for example. When nitrogen or low-boiling halocarbon is used as the inert gas for regeneration, roughly 80–90% of adsorbed compounds are desorbed in 8 hr at moderate temperature such as 120° C. A temperature in the range 100°–200° C. is convenient for commercial practice. The residual adsorbed compounds can be desorbed at higher temperature, 350° C., for example. Occasional complete desorption at such higher temperature is desirable to remove any buildup of impurities that are not desorbed at lower temperature.

Advantageously, the used bed of activated carbon can be regenerated by using an atmosphere of superheated steam. The superheated steam selectively reacts with PFIB adsorbed on the carbon to form $CF_3$—$CH_2$—$CF_3$ (HCFC-236fa) and carbonyl fluoride, thereby effectively completing the removal of PFIB from the gaseous stream by formation of a useful compound, the HCFC-236fa. This is an additional surprising aspect of the invention.

As will be illustrated by examples below, the recovery of useful products from a carbon bed used to remove PFIB from a mixed gaseous stream can be enhanced by regulating temperature, starting cold, e.g., at ambient temperature, and then increasing temperature to the desired elevated temperature. For example, regeneration can be carried out by sweeping nitrogen through the bed for several hours at low (e.g., ambient) temperature, and then, with nitrogen still flowing, heat the bed externally. As one skilled in the art will recognize, various temperature profiles can be followed to achieve the desired result. For example, the starting temperature for regeneration can be a fixed low temperature, such as a temperature of no more than about 75° C., for a fixed period of time, and then the temperature can be increased in discrete increments for discrete periods of time to reach a high temperature, such as a temperature of at least about 100° C. Preferably, the starting temperature is no more than about 50° C. Ambient temperature is especially convenient. In such a program, the temperature increments can vary and the time intervals can vary. Alternatively, temperature can start at the low value and increase uniformly to the high value, or the temperature can be increased smoothly following a profile that is variable with respect to time. One skilled in the art will also recognize that desorbtion time will be a function of temperature, with higher temperature resulting in shorter desorption time. Under such a procedure, PFIB remains on the carbon during the cold part of the sequence, but other compounds will be eluted (desorbed). If the gaseous stream is one from synthesis of TFE and HFP, most of the adsorbed TFE and HFP will be eluted during this part of the sequence, essentially free from PFIB, and the eluted products can be isolated for further separation and use. PFIB will be eluted after heating begins, along with other compounds that are not completely desorbed at the lower temperature, and by appropriate valving can be routed for further purification and/or destruction. For this mode of regeneration, an inert gas that is not halocarbon, e.g., nitrogen, promotes a better separation than a halocarbon, e.g., HCFC-22. However, the choice of inert gas may be governed by the overall system with which the PFIB removal system is used. Thus, if HCFC-22 is a component in the overall system, then HCFC-22 may be a better choice. As shown by example to follow, PFIB can be desorbed at ambient temperature when using HCFC-22 as the regenerating gas. This even suggests a totally low-temperature regeneration process, first using a gas such as nitrogen and then using a halocarbon such as HCFC-22.

In an attractive variation of this temperature-programmed regeneration, the cold part of the procedure can be carried out using an inert gas such as nitrogen, as above. Then, a flow of superheated steam can be started to complete the regeneration, with the steam serving as sweep gas, heat source, and reactant in the conversion of PFIB to HCFC-236fa. Alternatively, superheated steam can be used as the only regeneration gas, in which case all separations must be carried out downstream from the absorber. As one skilled in the art will recognize, the degree of conversion of PFIB to HCFC-236fa will depend on operating conditions during regeneration with superheated steam. Superheated steam is commonly available in commercial plants at temperatures in the range of 120°–200° C. (approximately), coinciding nicely with the above-recited temperature range that is convenient for regeneration.

To recover useful products adsorbed on the activated carbon, for example, TFE, HFP and perfluorocyclobutane if the gaseous stream is from pyrolysis of HCFC-22, a further concentration of PFIB can be achieved during regeneration by venting the saturated adsorber to a fresh adsorber. In such a scheme, the components will break through the fresh adsorber in the order of TFE, HFP, perfluorocyclobutane (dimer), and PFIB. Since, of these compounds, PFIB would break through last, the others can be recovered essentially free from PFIB. These steps, of course, can be iterated as many times as desired.

A preferred, but not the only, system for early PFIB removal from a gaseous stream employs a multiplicity of packed beds of activated carbon. This is illustrated, for example, by a system having four carbon beds. Two beds are used in series as adsorbers, with the second bed functioning as a guard bed. A third bed, previously used as first adsorber, is simultaneously being regenerated, with exiting gas going to the fourth bed. Unless superheated steam is used for regeneration, the fourth bed separates PFIB (for disposal) from other compounds. When the first bed has been in service for a predetermined time, or has adsorbed a predetermined load of compounds including PFIB, the first bed is removed from service and is regenerated, i.e., becomes the third bed. The second bed then becomes the first adsorber, and the regenerated bed, the original third bed, becomes the second adsorber.

EXAMPLE 1

Approximately 1.1 ml (0.45–0.5 g) of activated carbon (R3 Extra, Norit N.V.) was dried in a oven at 120° C. and 0.2 bar (20 kPa) absolute for 4 hr, then cooled under dry nitrogen, and packed in a 1.2 cm diameter tubular glass reactor. A cylinder containing approximately 0.02 vol % PFIB, 0.57–0.64 vol % HFP, 0.30–0.45 vol % TFE, approximately 0.04 vol % octafluorocyclobutane, 0.6–1.1 vol % HCl, and traces of other halogenated compounds in nitrogen was connected to the reactor through a needle valve and a flow measuring device. The flow rate was set to give a residence time in the carbon-filled volume of 4.5–5.5 sec. Temperature was 20°–22° C. (ambient) and pressure was 100 kPa absolute. Samples of the reactor exit gas were taken at hourly intervals and analyzed on a gas chromatograph (GC) with a detection limit for PFIB of 1 ppb ($10^{-9}$) by volume connected to a mass spectrometer. Analyses indicated that at least 98% of PFIB in the inlet gas was converted and/or adsorbed since no PFIB or HCFC-3281lmz was detected in the exit gas over a 12-hr period. No decrease of TFE or HFP concentration was detected.

The R3 Extra carbon is a hydrophobic carbon said to have few surface groups and having low magnesium and calcium content as measured by ash analysis (about 1 wt % ash). Micropore volume is about 45% of total pore volume. See Example 5.

EXAMPLE 2

R3 Extra activated carbon was dried in an oven at 110° C. and 0.3 bar (30 kPa) absolute for over 5 hr, with a small nitrogen flow to the oven to replace desorbed oxygen and some structural oxygen. A vertically positioned stainless steel pipe reactor having 5 cm diameter and 2 L volume was loaded with 0.5 kg (about 1.2L) of the dried carbon. A gas stream containing 3–4 vol % PFIB, 25–30 vol % HFP, 13–15 vol % TFE, 13–17 vol % octafluorocyclobutane, 29–36 vol % HCl, and other halogenated compounds totaling less than 10 vol % was fed to the carbon bed at flow rates in the range 4–36 L/hr corresponding to residence time in the range 18–2 min. Initial feed flow rate was 14 L/hr. Temperature was 25°–50° C. and pressure was approximately 120 kPa. During a 252 hr test period, 30–100% of the PFIB was removed from the gas stream by adsorption or reaction with HCl as determined by GC analysis of the exit gas from the reactor. No reaction of HCl with TFE or HFP was detected. Representative results given in Table 1 show that conversion varied with the residence time, with residence times in the range 5–10 min being most effective for removing/converting PFIB under the conditions of this test. For feed flow rates of 14 L/hr or less, flow rates were estimated from the pressure at the flow measuring device. The PFIB conversion figures are the sum of adsorption and conversion, both of which occurred, at least in the early part of the experiment. It was calculated that the cumulative amount of PFIB removed from the inlet gas stream during the test was about 2 kg, whereas the adsorption capacity of 0.5 kg of R3 Extra activated carbon for halogenated compounds is about 0.4 kg, which indirectly indicated that PFIB was converted during contact with the activated carbon.

TABLE 1

Flow Rates and PFIB Conversion for Example 2

| Time (hr) | Feed Flow (L/hr) | Residence Time (min) | PFIB Flow (L/hr) | PFIB Conversion (%) |
|---|---|---|---|---|
| 2.1 | 14 | 5.3 | 0.53 | 91 |
| 4.8 | 14 | 5.2 | 0.53 | 100 |
| 15.1 | 14 | 5.2 | 0.52 | 100 |
| 26.2 | 26 | 2.7 | 1.00 | 72 |
| 29.4 | 63 | 1.1 | 2.40 | 46 |
| 30.9 | 31 | 2.3 | 1.19 | 48 |
| 31.0 | 14 | 5.3 | 0.52 | 98 |
| 38.4 | 65 | 1.1 | 2.48 | 52 |
| 54.9 | 63 | 1.1 | 2.39 | 50 |
| 63.1 | 33 | 2.2 | 1.28 | 66 |
| 79.5 | 7 | 10.0 | 0.27 | 90 |
| 83.5 | 20 | 3.6 | 0.76 | 69 |
| 101.4 | 46 | 1.6 | 1.76 | 62 |
| 221.7 | 58 | 1.2 | 2.22 | 34 |
| 249.5 | 56 | 1.3 | 2.14 | 31 |

EXAMPLE 3

The reactor of Example 2 was used with a new charge of the same grade of activated carbon. Conditions and procedures followed were the same except for the following. The feed stream contained 4–5 vol % PFIB, 30–33 vol % HFP, 10.5–12 vol % TFE, 12–14.5 vol % octafluorocyclobutane, 30–35 vol % HCl, and other halogenated compounds making up the rest. Flow rate was 5–15 L/hr, corresponding to residence time in the range 14–5 min, and temperature was in the range 130°175° C. Test duration was 48 hr.

Throughout the test and under all conditions, PFIB was reduced to non-detectable levels either through adsorption or conversion. TFE and HFP were also partially converted under the conditions of this experiment. TFE was converted mainly to $CF_2H$—$CF_2Cl$. HFP was reduced, and is believed to have been converted to $CF_3$—$CFH$—$CF_2Cl$, as identified in Example 4. Conversions were approximately 25% for TFE and 75% for HFP, and both conversions decreased slowly with test time. Conversion of octafluorocyclobutane was not detected. These results indicate that higher process temperatures are suitable to remove PFIB from streams containing saturated compounds, but may not be suitable for streams containing desirable saturated compounds.

EXAMPLE 4

A 50/50 volume mixture of HFP and HCl was fed to the reactor of Example 1, with fresh charges of activated carbon, at a flow rate of 15 mL/hr and at several temperatures. The reaction product $CF_3$—$CFH$—$CF_2Cl$ was identified by GC mass spectrometry. Conversion of HFP was less than 1% at 20° C., and also less than 1% after 4 hr at 60° C., both with 6 g charges of carbon. Conversion of HFP was 4–8% at 128° C. with a 3 g charge of carbon. These results confirm the preference for lower process temperature to remove PFIB from a stream containing desirable unsaturated compounds.

EXAMPLE 5

The equipment of Example 1 was used to evaluate several grades of activated carbon (all obtained from Norit) for PFIB adsorption capacity. The carbons had different combinations of micropore volume (<2 nm), mesopore (2–100 nm) volume, and macropore (>100 nm) volume as indicated by benzene adsorption isotherm and mercury porosity measurements. Characteristics provided by Norit are summarized in Table 2, in which the names for grades C-Granular and Darco GD 4×12 are abbreviated. Bed porosity is the volume not accounted for by carbon skeleton and the identified pores, and is interpreted as the inter-particle space. Norit RB2 and Norit R3 Extra were also tested. Norit RX 3 Extra is R3 Extra without calcium and magnesium compounds; the pore structures are alike. The pore structure of Norit RB2 resembles that of R3 Extra. The procedures of Example 1 were followed, except that flow rate (14.5 mL/min) was set to give a residence time of about 4 sec and the pressure was about 1.1 bar (110 kPa) absolute. Results are summarized in Table 3, in which PFIB removed is the difference between concentration in the feed stream and concentration in the exit stream. As shown by these results, the activated carbons having higher proportions of micropores were more effective in removing PFIB.

TABLE 2

Characteristics of Carbons of Example 5

| Property | R3 Extra | ROX 0.8 | C-Gran. | Darco GD |
|---|---|---|---|---|
| Bulk density (g/L) | 419 | 397 | 208 | 443 |
| Carbon volume (mL/L) | 204 | 194 | 101 | 216 |
| Micropore vol. (mL/L) | 189 | 149 | 84 | 89 |
| Mesopore vol. (mL/L) | 32 | 62 | 149 | 144 |
| Macropore vol. (mL/L) | 191 | 246 | 260 | 202 |
| Total pore vol. (mL/L) | 412 | 457 | 493 | 435 |
| Micropore vol./Total pore | 0.46 | 0.33 | 0.17 | 0.20 |
| Bed porosity (mL/L) | 384 | 349 | 406 | 349 |

TABLE 3

Results for Example 5

| Carbon Type | Time (hr) | PFIB Removed (%) |
|---|---|---|
| C-Granular | 0.5 | 69 |
|  | 1.0 | 9 |
|  | 1.5 | 26 |

TABLE 3-continued

Results for Example 5

| Carbon Type | Time (hr) | PFIB Removed (%) |
|---|---|---|
| RX3 Extra | 0.5 | 99 |
|  | 1.0 | 97 |
|  | 2.0 | 98 |
| ROX 0.8 | 1.0 | 99 |
|  | 2.0 | 99 |
|  | 4.0 | 100 |
|  | 6.0 | 99 |
| Darco GD 4 × 12 | 1.0 | 80 |
|  | 2.0 | 62 |
|  | 4.0 | 29 |
|  | 5.0 | 46 |
| RB2 | 1.0 | 99 |
|  | 2.0 | 99 |
|  | 4.0 | 100 |
|  | 5.5 | 97 |
| R3 Extra | 1.0 | 95 |
|  | 2.0 | 99 |
|  | 4.0 | 93 |
|  | 5.0 | 95 |

EXAMPLE 6

The activated carbon used in the PFIB removal process of this invention can be regenerated as illustrated in this example and the following examples. Following an adsorption test in the equipment described in Example 2, with a charge of previously used and regenerated R3 Extra activated carbon, and using a similar halocarbon feed stream at 21° C. and 27 L/hr for approximately 20 hr (PFIB breakthrough at 4.3 hr), the feed stream was turned off. A flow of $CF_2HCl$ (HCFC-22) to the reactor at about 40 L/hr was turned on. Temperature was 19.2° C. at the start of regeneration as determined by a thermocouple in the center of the carbon bed. After 4.25 hr, reactor temperature had dropped to 15.2° C., at which point external heating of the reactor was started. The temperature increased slowly to 35.4° C. after 25 min, to 71.7° C. after 55 min, to 90.8° C. after 90 min, and to 103.4° C. after 170 min from the start of heating. The pressure in the reactor was in the range 1.7–2.0 bar (170–200 kPa) absolute. Reactor effluent was monitored by GC. At short times, HCFC-22 concentration in the effluent stream was less than the feed rate, presumably because it was adsorbed by the carbon as the adsorbed test compounds were displaced. By weighing the reactor before adsorption, after adsorption, and after regeneration, it was determined that the amount of halocarbon compounds adsorbed was 0.73 g/g (i.e., per gram of carbon), and the residue after regeneration was 0.39 g/g. From separate experiments it was estimated that the amount of HCFC-22 adsorbed during regeneration was about 0.19 g/g, which would be included in the 0.39 g/g residue, so the total amount of compounds desorbed was approximately 0.53 g/g. Results for compounds of interest are shown in FIG. 1, which shows that peak desorption of PFIB is slightly delayed relative to the other compounds. Note that essentially all of the desorbed compounds were desorbed before heating was started at the 4.25 hr point. By integrating the data for the compounds shown in FIG. 1 and for minor constituents, it was found that the volume concentration of PFIB in the desorbed mix was about 80% greater than in the feed stream, HCl neglected.

EXAMPLE 7

Figure 2:
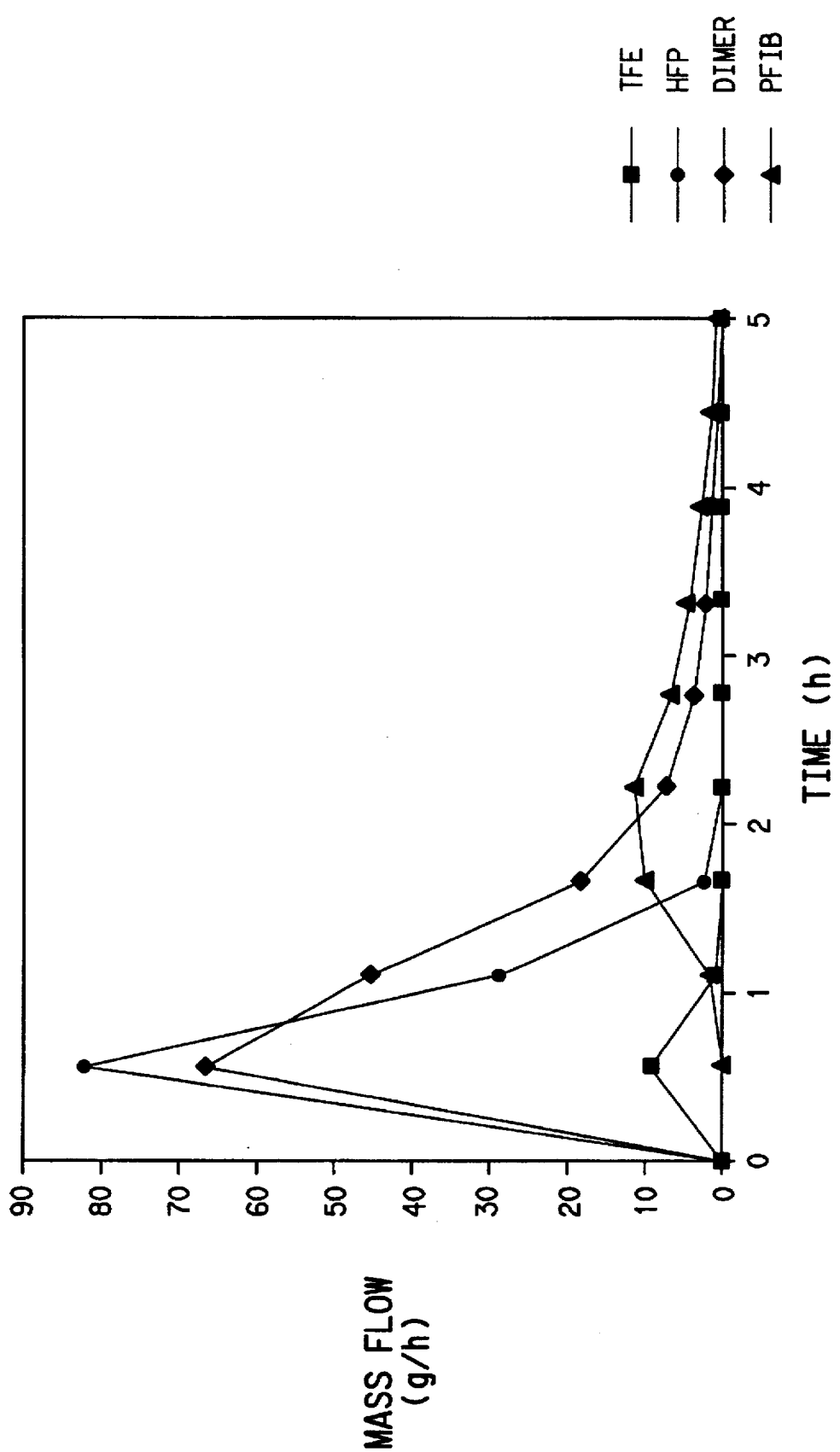
FIG. 2 shows the desorption profile for compounds adsorbed on activated carbon, using nitrogen as the regenerating gas, when heating of the carbon bed begins at the start of description (Example 7).

The procedure of Example 6 was generally repeated, except that a fresh charge of R3 Extra activated carbon was used, halocarbon feed stream flow rate was 50 L/hr, temperature for adsorption was approximately 25° C., adsorption test time was about 8 hr (PFIB breakthrough in 3.5 hr), and nitrogen was used as the regeneration gas at a feed flow rate of 21 L/hr and pressure was 180–200 kPa absolute. Regeneration temperature profile was slightly different, starting near ambient temperature and increasing to approximately 120° C. after 2.5 hr. Results for selected compounds are presented graphically in FIG. 2, which shows that PFIB elutes later than TFE, HFP, and octafluorocyclobutane when using nitrogen as the regeneration gas. This phenomenon can be used to separate PFIB from the other compounds during regeneration. By weighing the reactor before adsorption, after adsorption, and after regeneration, it was determined that the amount of halocarbon compounds adsorbed was 0.80 g/g, and the residue after regeneration was 0.20 g/g, so the desorbed compounds amounted to 0.60 g/g.

If superheated steam, e.g., at 170° C., is used as the regenerating gas, PFIB is converted to $CF_3CH_2CF_3$ (HFC-236fa) which is removed in the exit stream and recovered.

EXAMPLE 8

Figure 3:
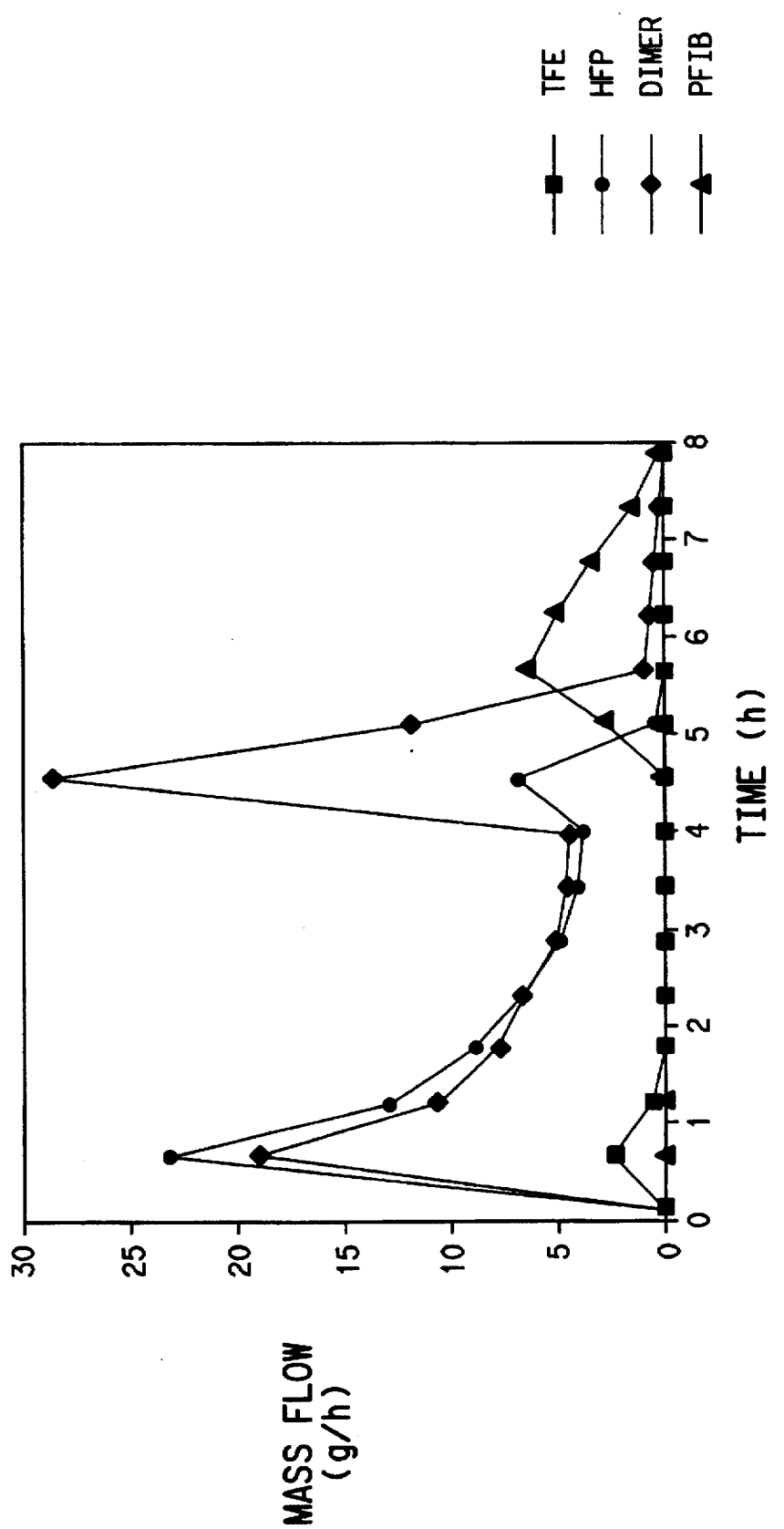
FIG. 3 shows the desorption profile for compounds adsorbed on activated carbon, using nitrogen as the regenerating gas, when heating of the carbon bed is preceded by a cold desorption period (Example 8).

The procedure of Example 7 was generally repeated, except that the activated carbon was previously used and regenerated R3 Extra, halocarbon feed stream flow rate was 90 L/hr, temperature for adsorption was approximately 30° C., adsorption test time was about 10 hr (PFIB breakthrough in about 3 hr), the nitrogen regeneration gas flow rate was 42 L/hr, and a different temperature profile was used for regeneration. In this instance, regeneration temperature was approximately 25° C. for the first 3.75 hr, and was then increased to 116° C. in 2.5 hr and held at this level thereafter. By weighing the reactor before adsorption, after adsorption, and after regeneration, it was determined that the amount of halocarbon compounds adsorbed was 0.78 g/g, and the residue after regeneration was 0.34 g/g, so the desorbed compounds amounted to 0.44 g/g. Results for selected compounds are presented graphically in FIG. 3. Most of the compounds desorbed partially during the initial cold part of the cycle. However, PFIB desorbed only during the hot part of the temperature profile. This is in contrast with the results of Example 6 in which HCFC-22 was used for regeneration. Thus, advantageously, a PFIB-free desorption stream can be obtained by a low-temperature inert purge with gas such as nitrogen.

If, instead of starting external heating at the 4 hr point of regeneration, a flow of superheated steam is introduced, PFIB is converted to HFC-236fa which is removed in the exit stream, along with any unconverted PFIB, and recovered.

What is claimed is:

1. A process for removing perfluoroisobutylene from a gaseous stream of halogenated compounds, comprising contacting the stream with dry activated carbon for a time sufficient to achieve effective removal of PFIB, whereby said perfluoroisobutylene is adsorbed by said activated carbon.

2. The process of claim 1 wherein the halogenated compounds include unsaturated compounds other than perfluoroisobutylene.

3. The process of claim 2 wherein the unsaturated compounds include at least one of tetrafluoroethylene and hexafluoropropylene.

4. The process of claim 3 wherein the temperature is from 10° to 60° C. and the residence time is 1–20 minutes.

5. The process of claim 1, and additionally contacting said activated carbon having said perfluoroisobutylene adsorbed thereon with superheated steam to form $CF_3CH_2CF_3$ and desorbing said $CF_3CH_2CF_3$ from said activated carbon.

6. The process of claim 5, wherein said contacting with superheated steam is preceded by contacting said activated carbon having said perfluoroisobutylene adsorbed thereon with halogen-free inert gas at low temperature.

7. The process of claim 6, wherein said halogen-free inert gas is nitrogen.

8. The process of claim 1, further comprising desorbing adsorbed halogenated compounds by a flow of inert gas, thereby regenerating said activated carbon.

9. The process of claim 8, wherein said inert gas is $CF_2HCl$ or nitrogen.

10. The process of claim 9, wherein said inert gas is nitrogen.

11. The process of claim 10, wherein said regenerating is carried out first at low temperature and then at high temperature.

12. The process of claim 11, wherein said high temperature is the result of using superheated steam as said inert gas.

13. The process of claim 1, wherein said stream includes HF and/or HCl to react with said adsorbed perfluoroisobutylene, and the product of said reaction is also adsorbed.

14. The process of claim 13, wherein HCl is present in said stream and the reaction between said HCl and said perfluoroisobutylene forms $(CF_3)_2$—CH—$CF_2Cl$.

15. The process of claim 13, and additionally desorbing from said activated carbon the product of the reaction between said HCl and/or HF and said perfluoroisobutylene.

16. The process of claim 13, wherein a plurality of halogenated compounds including said perfluoroisobutylene are adsorbed by said activated carbon and contacting said activated carbon with gas to sequentially desorb the adsorbed halogenated compounds from said activated carbon.

17. A process for converting perfluoroisobutylene to $CF_3CH_2CF_3$, comprising contacting said perfluoroisobutylene with superheated steam in the presence of activated carbon and forming said $CF_3CH_2CF_3$ as a result thereof.

18. The process of claim 17, wherein said perfluoroisobutylene is adsorbed on said activated carbon.

* * * * *